(12) United States Patent
Dausch

(10) Patent No.: US 7,449,821 B2
(45) Date of Patent: Nov. 11, 2008

(54) PIEZOELECTRIC MICROMACHINED ULTRASONIC TRANSDUCER WITH AIR-BACKED CAVITIES

(75) Inventor: David Edward Dausch, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 212 days.

(21) Appl. No.: 11/068,776

(22) Filed: Mar. 2, 2005

(65) Prior Publication Data

US 2006/0238067 A1  Oct. 26, 2006

(51) Int. Cl.
H01L 41/047 (2006.01)

(52) U.S. Cl. .............. 310/364; 310/322; 310/334; 310/365

(58) Field of Classification Search ................. 310/324, 310/334–335, 364, 365, 366
See application file for complete search history.

(56) References Cited

U.S. PATENT DOCUMENTS 6,246,158 B1 * 6/2001 Ladabaum ................. 310/334
6,551,248 B2 * 4/2003 Miller ........................ 600/459
6,608,383 B2 * 8/2003 Yokoyama et al. .......... 257/761
6,776,762 B2 * 8/2004 Erikson et al. .............. 600/459
6,909,221 B2 * 6/2005 Ayazi et al. ................. 310/321
7,109,633 B2 * 9/2006 Weinberg et al. ......... 310/313 B
7,132,780 B2 * 11/2006 Scott ....................... 310/316.01
2004/0027216 A1 * 2/2004 Ma et al. ..................... 333/187
2004/0049901 A1 * 3/2004 Nguyen ..................... 29/25.35
2004/0100163 A1 * 5/2004 Baumgartner et al. ........ 310/334
2005/0104204 A1 * 5/2005 Kawakubo et al. .......... 257/724
2006/0116585 A1 * 6/2006 Nguyen-Dinh et al. ...... 600/459

* cited by examiner

*Primary Examiner*—Darren Schuberg
*Assistant Examiner*—Derek J Rosenau
(74) *Attorney, Agent, or Firm*—Oblon, Spivak, McClelland, Maier & Neustadt, P.C.

(57) ABSTRACT

A piezoelectric micromachined ultrasonic transducer comprising a substrate and a first dielectric film formed on the substrate. An opening having a sidewall is formed through the substrate and first dielectric film. A bottom electrode is formed on the first dielectric film spanning the opening. A piezoelectric element is formed on the bottom electrode. A second dielectric film surrounds the piezoelectric element. A conformal insulating film is formed on the sidewall of the opening. A conformal conductive film is formed in contact with the bottom electrode and on the sidewall of the opening, wherein an open cavity is maintained in the opening. A top electrode is formed in contact with the piezoelectric element.

71 Claims, 7 Drawing Sheets

PIEZOELECTRIC MICROMACHINED ULTRASONIC TRANSDUCER WITH AIR-BACKED CAVITIES

TECHNICAL FIELD OF THE INVENTION

This invention relates to ultrasonic transducers and in particular piezoelectric micromachined ultrasonic transducers.

BACKGROUND OF THE INVENTION

Ultrasonic transducers are particularly useful for non-invasive as well as in vivo medical diagnostic imaging. Conventional ultrasonic transducers are typically fabricated from piezoelectric ceramic materials, such as lead zirconate titanate (PZT), or PZT-polymer composites, with the transducer material being diced or laser cut to form a plurality of individual elements arranged in one-dimensional or two-dimensional arrays. Acoustic lenses, matching layers, backing layers, and electrical interconnects (e.g., flex cable, metal pins/wires) are typically attached to each transducer element to form a transducer assembly or probe. The probe is then connected to control circuitry using a wire harness or cable, where the cable contains individual wires to drive and receive signals from each individual element. An important aim of ongoing research in ultrasonic transducer technology is increasing transducer performance and integrability with control circuitry while decreasing transducer size, power consumption and signal loss due to the cabling. These factors are particularly important for two-dimensional arrays required for three-dimensional ultrasound imaging.

The production of ever-smaller transducers is facilitated by micromachining techniques. There are two types of micromachined ultrasonic transducers (MUTs): capacitive MUTs (cMUTs) and piezoelectric MUTs (pMUTs). cMUTs operate by electrostatically actuating a suspended surface micromachined membrane via two opposing electrodes. Acoustic pressure is generated by vibrating the membrane, and received signals are measured as the membrane deflects proportional to the acoustic energy reflected back. pMUTs generate or transmit ultrasonic energy through application of ac voltage to the piezoelectric material causing it to alternately expand and contract, thereby flexing or vibrating the membrane. Received ultrasonic energy generates electrical charge in the piezoelectric layer due to vibrations of the bulk micromachined membrane.

Because pMUTs have a higher energy transduction mechanism, the piezoelectric layer, they generally have higher ultrasonic power capability than cMUTs. Thus, pMUTs transmit more ultrasonic energy and are more sensitive in receive for smaller element sizes compared to cMUTs. Elements in pMUT arrays also have higher capacitance (on the order of 100-1000 pF), so element impedance is lower and impedance mismatch to the cabling and electronics is less of an issue than for cMUT elements with capacitance on the order of 1 pF.

cMUTs can be energized by applying appropriate dc and ac voltage signals to the electrodes, such that an appropriate ultrasonic wave is produced. The dc voltage is required to electrostatically pull the membrane close to the substrate surface, thereby reducing the dielectric air gap, and the ac voltage vibrates the membrane to produce acoustic energy. Similarly, when electrically biased with dc voltage, the membrane of the cMUT may be used to receive ultrasonic signals by capturing reflected ultrasonic energy and transforming that energy into movement of the electrically biased membrane, which then generates a voltage signal. Another advantage of pMUTs is that they do not require the large (>100V) dc bias voltage for operation in addition to the ac signal. Lower ac voltages (<50V) are applied to activate the piezoelectric vibration for transmit, and receive signals are generated by the received ultrasonic energy alone (no applied voltage is required). One advantage of cMUTs is their higher bandwidth (>100%) over pMUTs (typically <50%) which provides higher frequency range of operation. This is beneficial for optimizing imaging resolution in different parts of the body which requires different frequency ranges.

A major advantage of MUTs is that they can be miniaturized and directly integrated with control circuitry. cMUTs with through-wafer via connections can be made by etching vias in a silicon wafer, coating the wafer with a thermal silicon dioxide for insulating regions and with polysilicon for electrical contacts, and then building up the cMUT membrane elements on the top surface of the wafer. Metal pads and solder bumps are deposited on the bottom surface of the wafer in order to solder the cMUT chip to semiconductor device circuitry. One disadvantage of such a device is that relatively high resistivity polysilicon, compared to metals, is used as the conductive material in the vias. Because of the very low signal strength (on the order of several mV or less) generated by cMUTs in the receive mode, the signal to noise ratio can be problematic during operation of the cMUT. Also, the low capacitance of cMUT elements produces high impedance, and therefore impedance mismatch with the electronics and cabling are greater which contributes to increased signal loss and noise. High resistance in the through-wafer vias further exacerbates the high element impedance problem. In addition, significant resistance in the vias will cause more power consumption and heat generation during operation when applying drive signals to cMUTs for transmit.

Another disadvantage of the cMUT device with polysilicon through-wafer interconnects is the processing temperature of forming the thermal silicon dioxide insulator and the polysilicon conductor. Processing temperatures for these steps are relatively high (600-1000° C.), thus creating thermal budget issues for the rest of the device. Because of these processing temperatures, the cMUT elements must be formed after the through-wafer vias are formed, and this sequence creates difficult processing issues when trying to perform surface micromachining on a substrate with etched holes through the wafer.

MUTs formed with through-wafer interconnects can be combined with control circuitry, thereby forming a transducer device, which can then be further assembled into a housing assembly including external cabling to form an ultrasonic probe. The integration of MUTs with control circuitry may significantly reduce the cabling required in the ultrasonic probe. The ultrasonic probe may also include various acoustic lens materials, matching layers, backing layers, and dematching layers. The housing assembly may form an ultrasonic probe for external ultrasound imaging, or a catheter probe for in vivo imaging.

Previously, joining a conventional ceramic ultrasonic transducer to electrical control circuitry required the use of many individual wires to connect each transducer element to the control circuitry. In the case of large transducer arrays, especially two-dimensional arrays having hundreds or more elements, large wiring harnesses were required. Large wiring harnesses drive up the cost and size of the ultrasonic probe, also making the probe difficult to manipulate by the user and impractical for use in catheter applications. Thus, it is desirable to reduce the cost and size of ultrasonic probes, especially for use in vivo.

One way of reducing the size of ultrasonic probes is to form the control circuitry on an integrated circuit assembly and attach the transducer directly to the integrated circuit.

SUMMARY OF THE INVENTION

There exists a need in the ultrasonic transducer art for miniaturized, space-efficient, low operating power ultrasonic transducers. There further exists a need in this art for smaller ultrasonic transducers that have higher signal/noise ratio, higher bandwidth, and better impedance match with electronics and cabling. There further exists a need in this art for ultrasonic transducers that more rapidly attenuate ultrasonic energy to reduce interelement crosstalk and unwanted reverberations. Furthermore, there exists a need in this art for ultrasonic transducers optimized for higher power transmission over a broader range of frequencies. In addition, there exists a need in this art for methodology of forming ultrasonic transducers with air-backed cavities and devices comprising ultrasonic transducers with air-backed cavities. There also exists a need in this art for methodology of forming integrated micromachined ultrasonic transducer devices at low temperatures.

These and other needs are met by embodiments of the present invention, which provide a piezoelectric micromachined ultrasonic transducer comprising a substrate. An opening is formed through the substrate. A bottom electrode is formed on the substrate spanning the opening. A piezoelectric element is formed on the bottom electrode. A conformal conductive film is formed in contact with the bottom electrode and on a sidewall of the opening. An open cavity is maintained in the opening.

These and other needs are further met by embodiments of the present invention, which provide a piezoelectric micromachined ultrasonic transducer comprising a substrate and a first dielectric film formed on the substrate. An opening having a sidewall is formed through the substrate and first dielectric film. A bottom electrode is formed on the first dielectric film spanning the opening. A piezoelectric element is formed on the bottom electrode. A second dielectric film surrounds the piezoelectric element, wherein top edges of the piezoelectric element are covered with the second dielectric film. A conformal insulating film is formed on the sidewall of the opening. A conformal conductive film is formed in contact with the bottom electrode and on the sidewall of the opening, wherein an open cavity is maintained in the opening. A top electrode is formed in contact with the piezoelectric element.

These and other needs are further met by embodiments of the present invention, which provide a piezoelectric micromachined ultrasonic transducer comprising a substrate. A plurality of openings having sidewalls is formed through the substrate. Spaced-apart bottom electrodes are formed on the substrate, wherein each spaced-apart bottom electrode spans one of the openings. Spaced-apart piezoelectric elements are formed on each of the bottom electrodes. A conformal conductive film is formed on each of the sidewalls. Each conformal conductive film is in contact with one or more of the bottom electrodes, wherein open cavities are maintained in each of the openings.

These and other needs are further met by embodiments of the present invention, which provide a method of forming a piezoelectric ultrasonic transducer comprising providing a substrate. A bottom electrode layer is formed on the substrate and a layer of piezoelectric material is formed on the bottom electrode layer. The bottom electrode layer and layer of piezoelectric material are patterned to form a plurality of spaced-apart bottom electrodes and spaced-apart piezoelectric elements on the substrate. An opening having sidewalls is formed through the substrate under each of the plurality of bottom electrodes exposing the bottom electrodes. A conformal conductive film is formed on the sidewalls and in contact with the bottom electrodes.

These and other needs are further met by embodiments of the present invention, which provide a vertically integrated piezoelectric micromachined ultrasonic transducer device comprising a substrate and a plurality of openings having sidewalls formed through the substrate. A first dielectric layer is formed on the substrate. Spaced-apart bottom electrodes are formed on the first dielectric layer. Each spaced-apart bottom electrode spans one of the plurality of openings. Spaced-apart piezoelectric elements are formed on each of the bottom electrodes. A conformal insulating film is formed on each of the sidewalls of the plurality of openings. A conformal conductive film is formed on each of the conformal insulating films. Each conformal conductive film is in contact with one or more of the bottom electrodes and an open cavity is maintained in each of the openings. A ground pad is formed on the substrate. A second dielectric film is formed between the piezoelectric elements. A top electrode is formed in contact with the piezoelectric elements and the ground pad. A semiconductor device is attached to the ultrasonic transducer and the conformal conductive film is electrically connected to the semiconductor device.

In addition, these and other needs are met by embodiments of the present invention, which provide a method of forming a vertically integrated piezoelectric ultrasonic transducer device comprising providing a substrate and forming a first dielectric layer on the substrate. A bottom electrode layer is formed on the first dielectric layer and a layer of piezoelectric material is formed on the bottom electrode layer. The bottom electrode layer and layer of piezoelectric material are patterned to form a plurality of spaced-apart bottom electrodes and spaced-apart piezoelectric elements on the substrate. A ground pad is formed on the substrate. A second dielectric layer is formed between the piezoelectric elements. A top electrode is formed in contact with the piezoelectric element and the ground pad. Openings having sidewalls are formed through the substrate under each of the spaced apart bottom electrodes and piezoelectric elements. A conformal insulating layer is formed on the sidewalls of the openings. A conformal conductive layer is formed on the conformal insulating layer and in contact with each of the bottom electrodes. A semiconductor device is attached to the ultrasonic transducer through the conformal conductive layer.

This invention addresses the needs for improved, smaller micromachined ultrasonic transducers and transducer arrays that have higher bandwidth, higher signal to noise ratio, better impedance match and require less energy to operate. This invention further addresses the need for a micromachined ultrasonic transducer that produces higher ultrasonic power and is more sensitive to received ultrasonic energy for smaller element sizes. Furthermore, this invention addresses the need for an ultrasonic transducer that more rapidly attenuates spurious ultrasonic energy. In addition, this invention addresses the need for methodology of forming integrated micromachined ultrasonic transducer devices at low temperatures.

The foregoing and other features, aspects, and advantages of the present invention will become apparent in the following detailed description of the present invention when taken in conjunction with the accompanying drawings.

DETAILED DESCRIPTION OF THE INVENTION

The invention will be described in conjunction with the formation of the pMUT devices illustrated in the accompanying drawings. However, this is exemplary only as the claimed invention is not limited to the formation of the specific devices illustrated in the drawings.

Figure 1A:
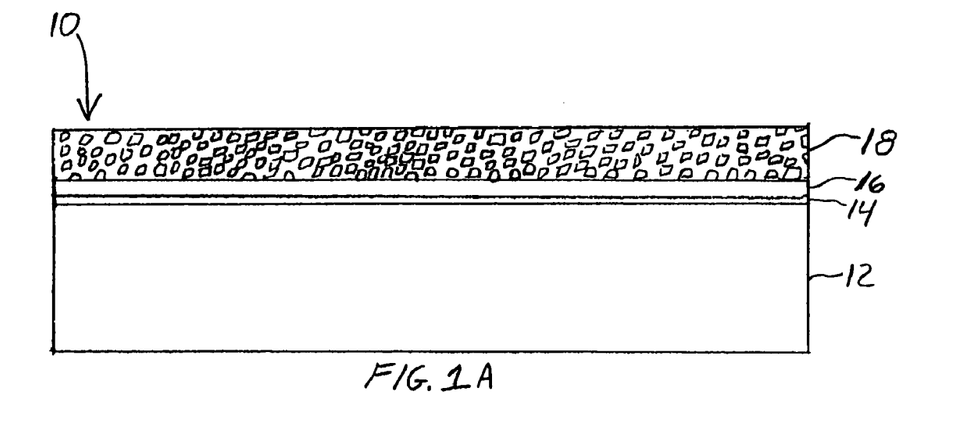
FIGS. 1-8 illustrate the formation of a piezoelectric micromachined ultrasonic transducer device wherein the transducer is attached to a semiconductor device via solder bumps according to an embodiment of the invention.

A method of forming a vertically integrated pMUT device according to certain embodiments of the present invention is described. A pMUT device structure 10 comprising a substrate 12 is provided, as illustrated in FIG. 1A. According to certain embodiments of the present invention, the substrate 12 is a silicon wafer. A first dielectric film 14 is formed on the substrate 12. In certain embodiments of the present invention, the first dielectric film 14 comprises silicon oxide or silicon nitride. A bottom electrode layer 16 is formed overlying the first dielectric film 14. According to certain embodiments of the present invention, the bottom electrode layer 16 can comprise a metal or conductive metal oxide. A layer of piezoelectric material 18 is subsequently formed over the bottom electrode layer.

Piezoelectric materials that can be used in the present invention are ceramics including ZnO, AlN, LiNbO$_4$, lead antimony stannate, lead magnesium tantalate, lead nickel tantalate, titanates, tungstates, zirconates, or niobates of lead, barium, bismuth, or strontium, including lead zirconate titanate (Pb(Zr$_x$Ti$_{1-x}$)O$_3$ (PZT)), lead lanthanum zirconate titanate (PLZT), lead niobium zirconate titanate (PNZT), BaTiO$_3$, SrTiO$_3$, lead magnesium niobate, lead nickel niobate, lead manganese niobate, lead zinc niobate, lead titanate. Piezoelectric polymer materials such as polyvinylidene fluoride (PVDF), polyvinylidene fluoride-trifluoroethylene (PVDF-TrFE), or polyvinylidene fluoride-tetrafluoroethylene (PVDF-TFE) can also be used. According to certain embodiments of the present invention, the layer of piezoelectric material is PZT.

The piezoelectric material 18 can be deposited on the pMUT device structure 10 by physical vapor deposition (PVD), such as sputtering, chemical vapor deposition (CVD), molecular beam epitaxy (MBE), or by a spin coating a sol gel. In certain embodiments of the present invention, an organic solution containing lead subacetate, zirconium acetate, and titanium acetyl acetonate is spun onto a pMUT device structure 10, and the acetate film is pyrolized and annealed to form the PZT layer 18.

Figure 1B:
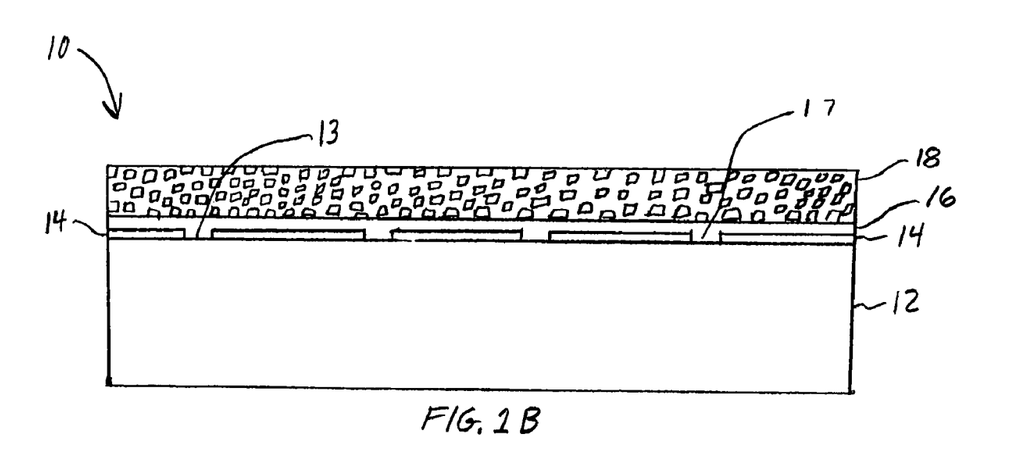

In certain embodiments of the present invention, spaced-apart vias 27 are formed by etching from the front side 13 of the substrate 12 through the first dielectric film 14 prior to deposition of the bottom electrode layer 16, as illustrated in FIG. 1B, to provide a path for electrical connection between subsequently formed spaced-apart bottom electrodes and through wafer interconnects.

Figure 2:
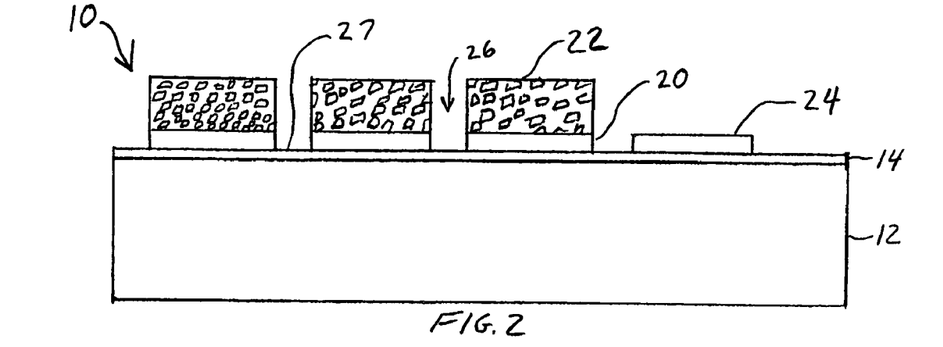

The pMUT device structure 10 is subsequently patterned, as illustrated in FIG. 2, by etching the layer of piezoelectric material 18 and bottom electrode layer 16 to form an array of piezoelectric elements 22 and bottom electrodes 20. The array of piezoelectric elements 22 can be formed by conventional photolithographic techniques, such as photoresist deposition, selective exposure, development, chemical or reactive ion etching, and subsequent removal of the exposed piezoelectric and electrode materials, according to certain embodiments of the present invention. In certain embodiments of the present invention, anisotropic etching, such as a plasma etch, is performed to provide openings 26 exposing the upper surface of the first dielectric film 14. In other embodiments of the present invention, a metal liftoff process is used to pattern the bottom electrode prior to deposition of the piezoelectric material. During etching to form the separate piezoelectric elements 22, one of the piezoelectric elements on the periphery of the pMUT device structure 10 is further etched to remove the piezoelectric material 18 from the bottom electrode 20 forming a ground pad 24. In certain embodiments of the present invention, only one ground pad 24 is needed per pMUT device 10. In other embodiments of the present invention, multiple ground pads are provided for redundant electrical connection.

Figure 3:
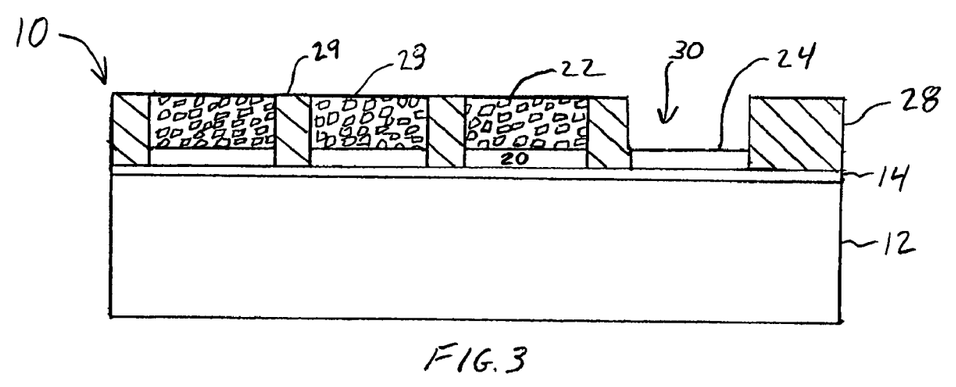

A second dielectric film 28 providing acoustic and electrical isolation between the piezoelectric elements 22 is formed on the pMUT device structure 10 filling the openings 26. As illustrated in FIG. 3, the second dielectric film 28 is planarized so that its upper surface 29 is substantially planar with the upper surface 23 of the piezoelectric elements 22. The second dielectric film 28 is removed above the ground pad 24, such as by etching or photolithography, forming an opening 30. The second dielectric film 28 can be a polymer. In certain embodiments of the present invention, the second dielectric film 28 is a polyimide, parylene, polydimethylsiloxane (PDMS), polytetrafluoroethylene (PTFE) or a polybenzocyclobutene (BCB). The use of a polymer as the second dielectric film 28 reduces inter-element cross talk in piezoelectric transducer arrays compared with bulk ceramic arrays that do not have the polymer layer between the elements. The polymer dielectric 28 attenuates acoustic energy between the elements 22 so that the vibration from one piezoelectric element 22 does not affect adjacent piezoelectric elements 22. Low interelement crosstalk has been demonstrated in two-dimensional pMUT arrays by employing a polymer dielectric film. Crosstalk as low as −50 dB has been measured, compared to much higher crosstalk of −20 dB for PZT ceramic two-dimensional arrays with no polymer dielectric between the piezoelectric elements.

Figure 4:
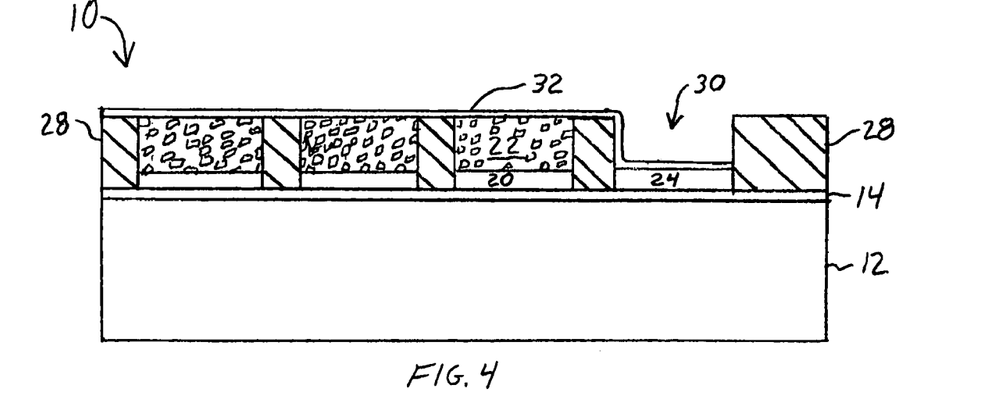

A top electrode 32 is formed overlying the piezoelectric element 22, second dielectric film 28, and the ground electrode 24, as illustrated in FIG. 4. According to certain embodiments of the present invention, the top electrode 32 comprises a metal. According to certain embodiments of the present invention, the top electrode 32 connects each piezoelectric element 22 to the ground pad 24.

Figure 5:
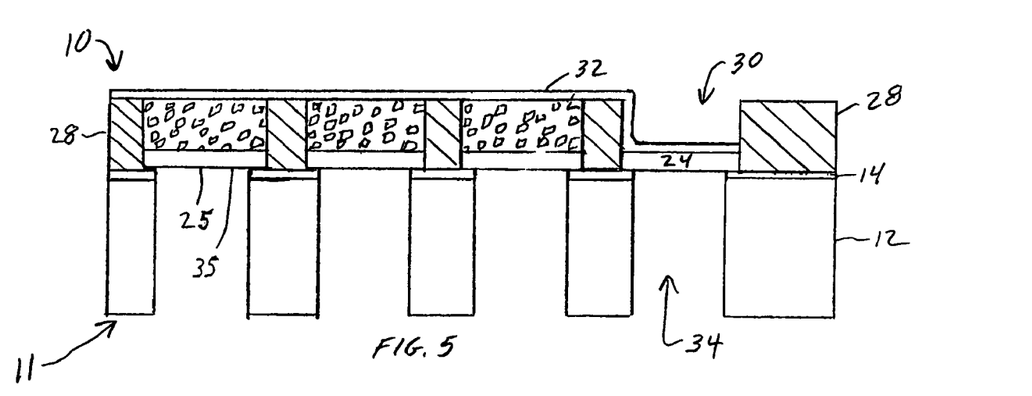

The back side of the pMUT device structure 11 is selectively etched to form through-wafer vias 34 exposing the bottom surface of the bottom electrodes 25 forming piezoelectric membranes 35 comprising the bottom electrodes 24 and the piezoelectric elements 22, as shown in FIG. 5. Anisotropic etching through the substrate 12 and first dielectric film 14 is performed using the photolithographic patterning techniques described above and appropriate chemical etchants for silicon wafers 12 and the first dielectric film 14 to form the through-wafer vias 34, according to certain embodiments of the present invention. According to certain embodiments of the present invention, photolithographic processes and deep reactive ion etching (DRIE) using an inductively coupled plasma (ICP) reactor is used to etch the substrate 12 and first dielectric film 14 forming through-wafer vias 34 with vertical sidewalls 37 in the vias. The advantage of the DRIE process is that higher density arrays can be formed compared with anisotropic chemical etching, and diverse geometric element shapes can be formed.

For pMUT structures in which the through-wafer vias 34 are formed using a DRIE process, substantial freedom of geometrical element shape is afforded. Because anisotropic chemical etching follows the crystallographic planes in silicon, elements formed by this method are limited to square and rectangular shapes. Elements formed by DRIE can be circular, square, rectangular, or other polygonal shapes. Circular shaped elements provide stronger ultrasonic response at a single resonance frequency. However, for applications requiring higher bandwidth, square, rectangular or polygonal (e.g., hexagonal, octagonal) shaped elements provide multiple overtones in the frequency response due to different dimensions in different geometrical directions. These overtones increase the frequency range or bandwidth of the device, although at a slight decrease in sensitivity per unit area. Bandwidth has been measured for pMUT elements with circular shape and was found to be only 15-20%, whereas square elements produced measured bandwidth in the range of 50-80%. The circular elements, however, possessed 20-30% higher sensitivity per unit area than the square elements.

Additionally, square, rectangular or polygonal shaped elements can be supported by the substrate on all sides or only some of the sides by extending the DRIE etch beyond the unsupported edges. For example, a square element can be supported on all four edges by the substrate, or can be supported only on two edges and unclamped on the other two edges. In this way, the piezoelectric membrane is made more flexible for larger vibrational amplitude. Circular elements are generally supported around the entire circumference. Rectangular elements with large aspect ratios (10:1 or greater) can be formed and are generally preferable for one-dimensional pMUT arrays, whereas elements with smaller aspect ratios (closer to 1:1, e.g., square or nearly square, hexagonal, octagonal, circular) are typically formed for two-dimensional pMUT arrays.

Figure 6:
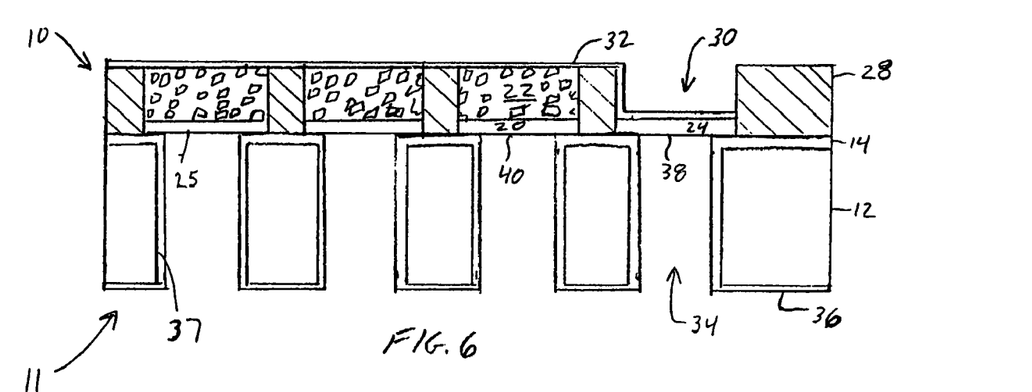

Adverting to FIG. 6, a conformal insulating film 36 is deposited on the back side of the pMUT device structure 11, including sidewalls 37 of the through-wafer vias 34. The portion of the conformal insulating film 36 covering the bottom surfaces 25, 38, and 40 of the bottom electrodes 20 and 24 is subsequently removed, such as by etching. The conformal insulating film 36 can comprise conventional dielectrics such as a vapor-deposited polymer, oxide or nitride material. The conformal insulating film 36 is deposited by a low temperature vapor deposition process, such as PVD or CVD. Exposing the bottom surface 25 of the bottom electrodes allows electrical connection to the bottom electrode 24 of the piezoelectric membrane 35 without compromising the electrical isolation of the multiple through-wafer vias 34.

Figure 7A:
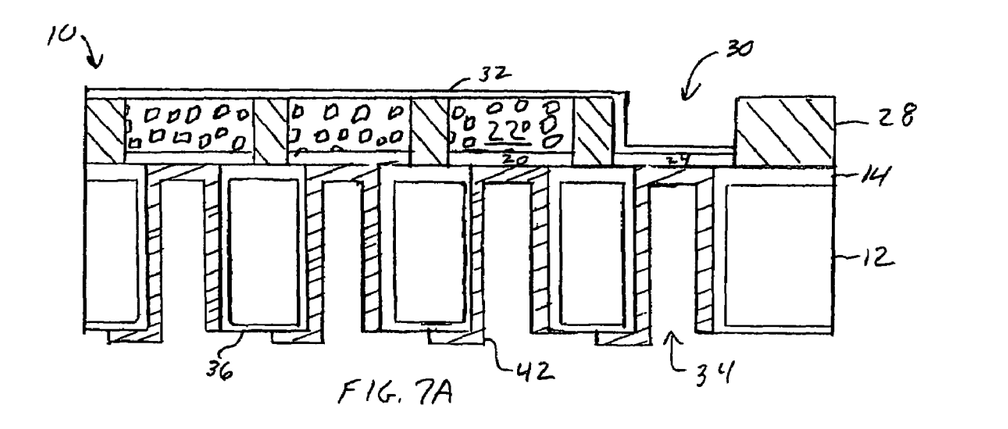

A conformal conductive film 42 is subsequently formed on the back side of the pMUT device structure 11. The conformal conductive film 42 is subsequently patterned such that the individual through-wafer vias 34 are electrically isolated from one another and from the ground contact 24, as illustrated in FIG. 7A. According to certain embodiments of the present invention, conformal conductive film 42 comprises a metal. The conformal conductive film 42 can be patterned by conventional photolithographic techniques to create through-wafer interconnects 42 in the through-wafer vias 34. In other embodiments of the present invention, multiple through-wafer interconnects 42 can be electrically connected to form larger subsets of elements that can be addressed simultaneously. These larger element subsets are electrically isolated from the ground via 30. For example, one-dimensional arrays can be formed by connecting rows of elements in a two-dimensional array.

A conformal conductive film 42 is subsequently formed on the back side of the pMUT device structure 11. The conformal conductive film 42 is subsequently patterned such that the individual through-wafer vias 34 are electrically isolated from one another and from the ground contact 24, as illustrated in FIG. 7A. According to certain embodiments of the present invention, conformal conductive film 42 comprises a metal. The conformal conductive film 42 can be patterned by conventional photolithographic techniques to create through-wafer interconnects 42 in the through-wafer vias 34. In other embodiments of the present invention, multiple through-wafer interconnects 42 can be electrically connected to form larger subsets of elements that can be addressed simultaneously. These larger element subsets are electrically isolated from the ground via 33. For example, one-dimensional arrays can be formed by connecting rows of elements in a two-dimensional array.

Suitable metals for use as the bottom electrode 16, top electrode 32, and conformal conductive film 42 include: Cr/Au, Ti/Au, Ti/Pt, Au, Ag, Cu, Ni, Al, Pt, In, Ir, $IrO_2$, $RuO_2$, $In_2O_3$:$SnO_2$ (ITO) and $(La, Sr)CoO_3$ (LSCO). Suitable techniques for depositing the metals for the bottom electrode layer 14, top electrode 32, and conformal conductive film 42 include CVD, PVD, electroplating, electroless plating and electron beam evaporation techniques. According to certain embodiments of the present invention, the bottom electrode layer 16 comprises Ti/Pt, Ir, $IrO_2$, $RuO_2$, or LSCO. According to certain embodiments of the present invention, the conformal conductive film 42 comprises CVD Cu, electroplated Cu, or electroless Ni or Au.

Figure 7B:
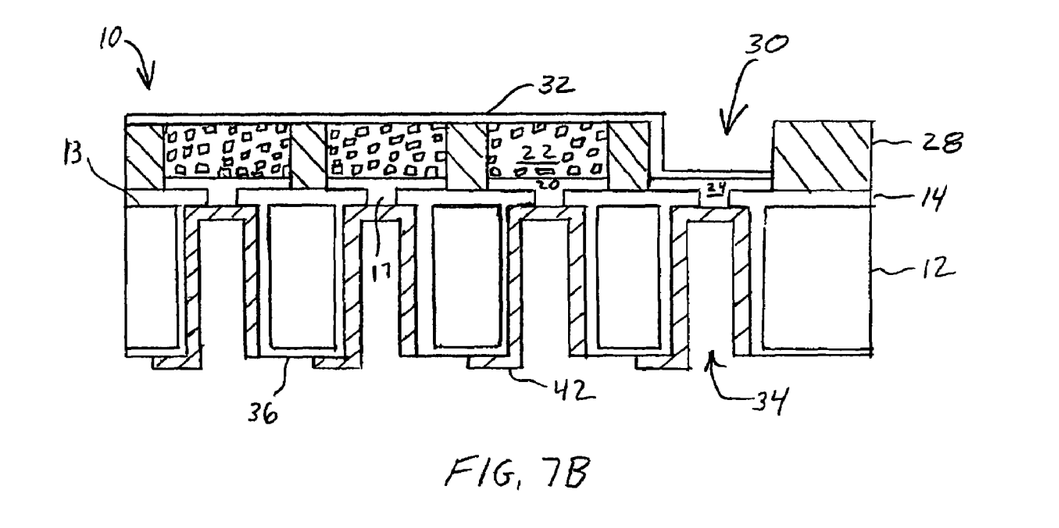

In other embodiments of the present invention, as shown in FIG. 7B, only the substrate 12 is etched forming through-wafer vias 34 wherein the etch stops at the first dielectric layer 14 exposing spaced-apart vias 17. The spaced-apart vias 17 were previously formed by etching from the front side 13 of the substrate 12 through the first dielectric film 14. The spaced-apart vias 17 are exposed again when the conformal insulating film 36 is etched, and provide electrical connection between the spaced-apart bottom electrodes 20 and the subsequently formed interconnects 42.

Figure 8:
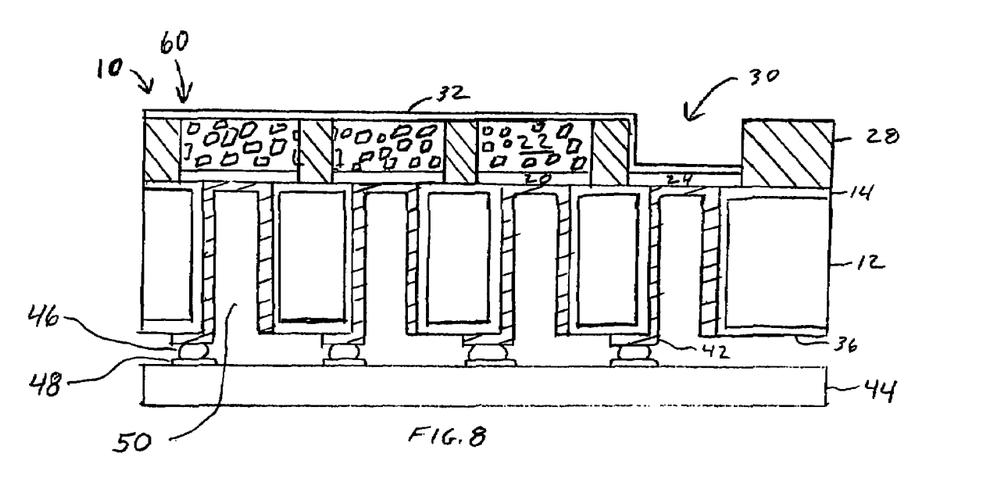

Adverting to FIG. 8, the pMUT device structure 10 is connected to a semiconductor device 44 to form a vertically integrated pMUT device 60. In certain embodiments of the present invention, the connection is made through solder bumps 46 connecting the conformal conductive layer 42 to solder pads 48 on the semiconductor device 44. The patterned through-wafer interconnects 42 provide direct electrical connection from the piezoelectric membranes 35 to the semiconductor device 44. The attachment of the semiconductor device 44 to the pMUT device structure 10 creates air backed cavities 50. The air-backed cavities 50 provide optimum acoustic performance. The air-backed cavity 50 allows greater vibration in the piezoelectric membrane 35 with minimal acoustic leakage compared to surface micromachined MUTs. Vibrational energy from surface micromachined membranes can be dissipated into the bulk silicon substrate which resides directly below the membrane thus limiting the ultrasonic transmit output and receive sensitivity. The air backed cavity 50 of the present invention reduces or eliminates this energy dissipation since the vibrating membrane 35 does not reside directly on or over the bulk substrate 12.

The semiconductor device 44 can be any semiconductor device known in the art, including a wide variety of electronic devices, such as flip-chip package assemblies, transistors, capacitors, microprocessors, random access memories, etc. In general, semiconductor devices refer to any electrical device comprising semiconductors. In certain embodiments of the present invention, the semiconductor device 44 is a CMOS chip.

Because each piezoelectric element 22 is electrically isolated from adjacent piezoelectric elements 22, the individual elements can be separately driven in the transducer transmit mode. Additionally, receive signals can be measured from each piezoelectric membrane 35 independently by the semiconductor device 44.

An advantage of the formation of the through-wafer interconnects 42 is that separate wires, flex cable, etc., are not required to carry electrical transmit and receive signals between the membranes 35 and semiconductor device 44, as electrical connection is provided directly by the interconnects 42. This reduces the number of wires and size of the cabling required to connect the ultrasonic probe to a control unit. Furthermore, the shorter physical length of the through-wafer interconnects 42 (on the order of 100 μm to a few mm) compared with conventional cable or wire harnesses (length on the order of meters) provides connections with lower resistance and shorter signal path which minimizes loss of the transducer receive signal and lowers the power required to drive the transducers for transmit.

The use of metal interconnects 42 and electrodes 20, 32 provide a piezoelectric device with higher electrical conductivity and higher signal-to-noise ratio than devices using polysilicon interconnects and electrodes. In addition, the use of low temperature processes of depositing the conformal insulating layer 36 and conformal conductor 42 reduces the thermal budget of the device processing, thus limiting the damaging effects of excessive exposure to heat. This also allows the pMUT elements 22 to be formed before etching the through-wafer via holes 34 in the substrate, thus simplifying the overall processing.

Figure 9:
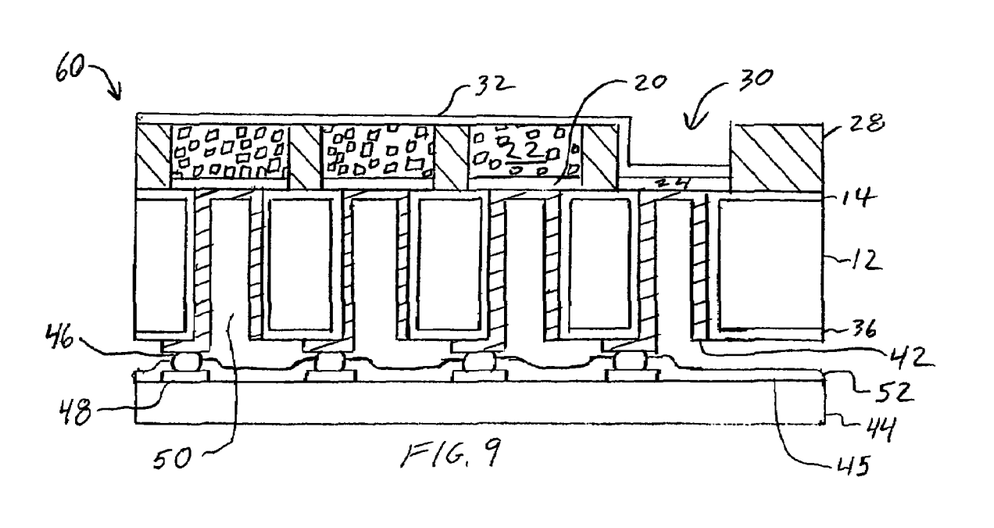
FIG. 9 illustrates an embodiment of the invention wherein a polymer film is formed on a surface of a semiconductor device facing open cavities.

In certain embodiments of the present invention, a polymer coating 52 is formed on the surface of the semiconductor device 45, or at the base of the air-backed cavity 50, as shown in FIG. 9. The polymer layer 52 attenuates acoustic energy reflected from the piezoelectric membrane 35. When a pMUT device structure 10 is attached directly to a semiconductor device substrate 44, there is observed some reverberation of the pMUT element 22 as acoustic energy is reflected off of the semiconductor device substrate 44 and directed back toward the piezoelectric membrane 35. The reverberation causes noise in the pMUT signal and reduces ultrasound image quality. Also the acoustic energy could affect semiconductor device operation by introducing noise in the circuit. Without the polymer attenuating layer 52, a resonant cavity condition is created which causes excessive ringing or reverberations in the transducer membrane 35. By providing a polymer layer 52 on top of the semiconductor device 44 or at the base of the air-backed cavity 50, acoustic energy reflected from the pMUT device structure 10 is attenuated by the polymer layer 52. The polymer layer 52 has lower acoustic impedance and therefore reflects less ultrasonic energy than a bare silicon surface of the semiconductor device with high acoustic impedance. In certain embodiments of the present invention, the polymer layer 52 can also function as an adhesive for attachment of the pMUT device structure 10 to the semiconductor device 44. In certain embodiments of the present invention, the polymer layer 52 comprises an epoxy.

The thickness of piezoelectric elements 22, in certain embodiments of the present invention, can range from about 0.5 μm to about 100 μm. In certain embodiments of the present invention, the thickness of the piezoelectric elements 22 ranges from about 1 μm to about 10 μm. The width or diameter of the piezoelectric elements 22 can range from about 10 μm to about 500 μm with center-to-center spacing from about 15 μm to about 1000 μm. In certain embodiments of the present invention, the width or diameter of the piezoelectric elements 22 can range from about 50 μm to about 300 μm with center-to-center spacing from about 75 μm to 450 μm for ultrasonic operation in the range of 1 to 20 MHz. In other embodiments of the present invention, smaller elements of less than 50 μm can be patterned for higher frequency operation of >20 MHz. In this case, multiple elements may be electrically connected together to provide higher ultrasonic energy output while still maintaining the high frequency of operation.

The thickness of the first dielectric film 14, in certain embodiments of the present invention, can range from about 10 nm to about 10 μm. In certain embodiments of the present invention, the thickness of the conformal insulating film 36 ranges from about 10 nm to about 10 μm. The thickness of the bottom electrode 20, top electrode 32, and conformal conductive layer 42 ranges from about 20 nm to about 25 μm. The depth of the open cavity 50, in certain embodiments of the present invention, can range from about 100 μm to several mm.

Figure 10:
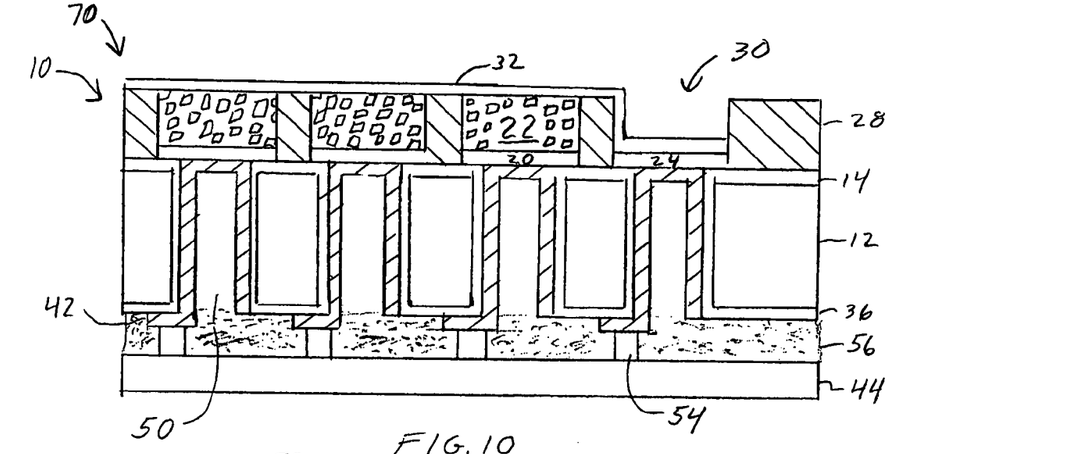
FIG. 10 illustrates an embodiment of the invention wherein the transducer is connected to a semiconductor device via plated metal contacts.

In certain embodiments of the present invention the pMUT device structure 70 is connected to the semiconductor device 44 through metal contacts 54 formed in the epoxy layer 56 on the semiconductor device 44, as illustrated in FIG. 10. The epoxy layer 56, in addition to functioning as an acoustic energy attenuator, also functions as an adhesive for adhering the pMUT device structure 10 to the semiconductor device 44. The epoxy layer 56 can be patterned using photolithographic and/or etching techniques, and metal contacts can be deposited by electroplating, sputtering, e-beam evaporation, CVD, or other deposition methods.

Figure 11:
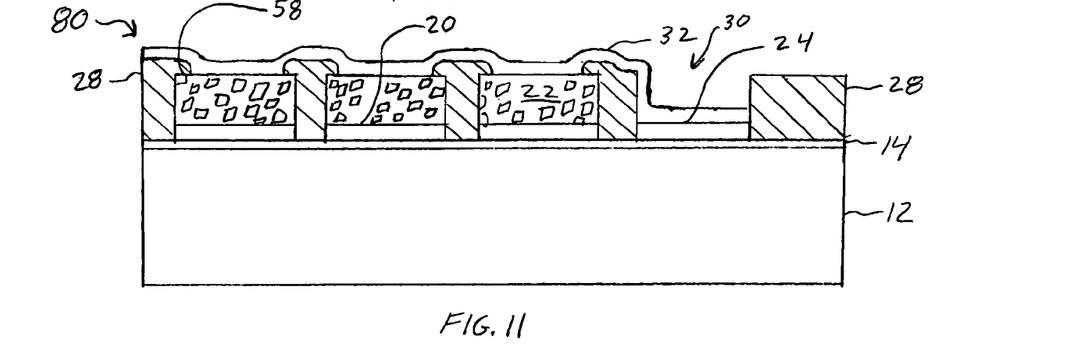
FIGS. 11 and 12 illustrate an embodiment of the invention wherein a dielectric film formed between the piezoelectric elements is disposed on the top edges of the piezoelectric elements.
Figure 12:
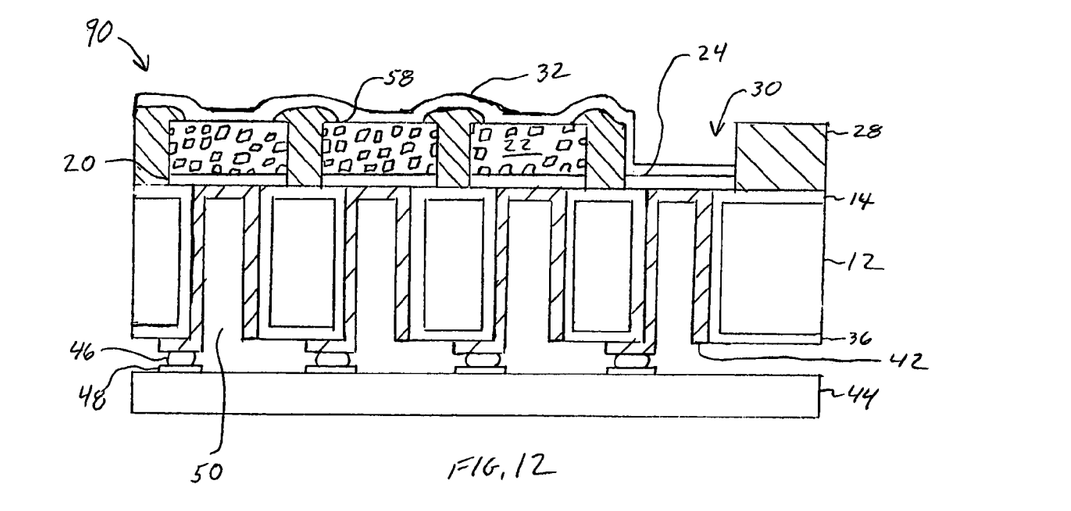

The second dielectric film 28 is disposed on the top edges 58 of the piezoelectric elements in certain embodiments of the present invention, as illustrated in FIG. 11. The pMUT device structure 80 is subsequently processed, including back side etching, as previously described and connected to a semiconductor device 44 to form a vertically integrated piezoelectric micromachined ultrasonic transducer device 90, as illustrated in FIG. 12. The second dielectric film 28 on the top edges of the patterned piezoelectric layer 58 provides improved electrical isolation of the two electrodes 32, 20 connected to the piezoelectric elements 22. This embodiment helps account for any photolithography misalignment which could inadvertently cause a gap between the polymer dielectric 28 and piezoelectric layer 22 edges causing the top electrode 32 to short to the bottom electrode 20. It also eliminates the need for any planarization processes that might be required in other embodiments. This embodiment further provides a method of forming a size or shape of the top electrode 32 that is different from the size and shape of the patterned piezoelectric layer 22. If thick enough (on the order of the piezoelectric thickness), the polymer dielectric 28 with much lower dielectric constant than the piezoelectric layer 22 causes the voltage applied to the pMUT 90 device to primarily drop only across the dielectric, thus electrically isolating the portion of the piezoelectric layer 58 that is covered with the dielectric. The effective shape of the piezoelectric element 22 with regard to the applied voltage is only the portion of the piezoelectric layer 22 that is not covered with the dielectric. For example, if it is desired only to electrically activate 50% of the total piezoelectric geometrical area, then polymer dielectric 28 can physically cover and electrically isolate the remaining 50% of the piezoelectric area and prevent it from being activated. Also if a complex electrode pattern is desired such as an interdigitated structure, the polymer dielectric 28 can be patterned to provide the interdigitated structure. This is important for certain embodiments wherein the top electrode 32 is a continuous ground electrode across the entire pMUT array 90. Simpler processing is provided by creating the electrically active area by patterning the polymer dielectric 28, thus the active area assumes the shape of the top electrode area contacting the piezoelectric film 16, rather than patterning the bottom electrode 20 and piezoelectric film 16.

Figure 13:
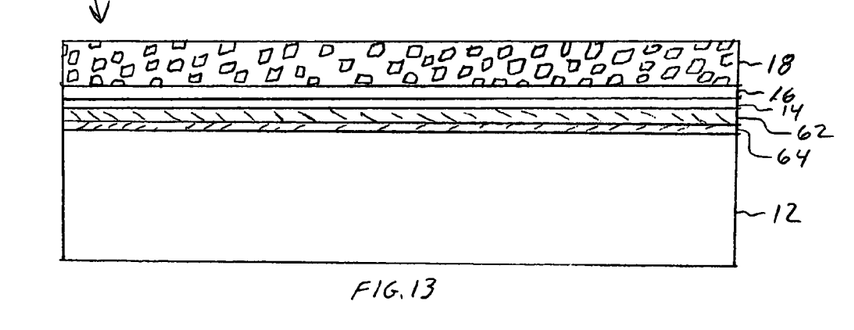
FIGS. 13-15 illustrate the formation of a piezoelectric micromachined ultrasonic transducer device wherein the piezoelectric elements are formed on a silicon-on-insulator substrate.

Certain embodiments of the present invention use a silicon-on-insulator (SOI) substrate as the substrate. As shown in FIG. 13, a substrate 12, such as a silicon wafer, is provided with a thin silicon layer 62 overlying a buried silicon dioxide layer 64 formed on the substrate 12. A first dielectric film 14 is formed overlying the silicon layer 62 and a bottom electrode layer 16 is formed overlying the first dielectric film. A layer of piezoelectric material 18 is formed overlying the bottom electrode layer 16 to provide a SOI pMUT device structure 100. Advantages of using the SOI substrate include better control of the DRIE etch using the buried oxide as the silicon substrate etch stop. This also provides better control of the pMUT membrane 35 thickness for better control and uniformity of the resonance frequencies of the individual elements in an array, as the membrane thickness is defined by the thickness of the thin silicon layer of the SOI substrate 62. According to certain embodiments of the present invention, the thin silicon layer 62 has thickness of about 200 nm to 50 μm, and the buried oxide layer 64 has thickness of about 200 nm to 1 μm. In other embodiments of the present invention, the thin silicon layer 62 has thickness of about 2 μm to 20 μm, and the buried oxide layer 64 has thickness of about 500 nm to 1 μm.

Figure 14:
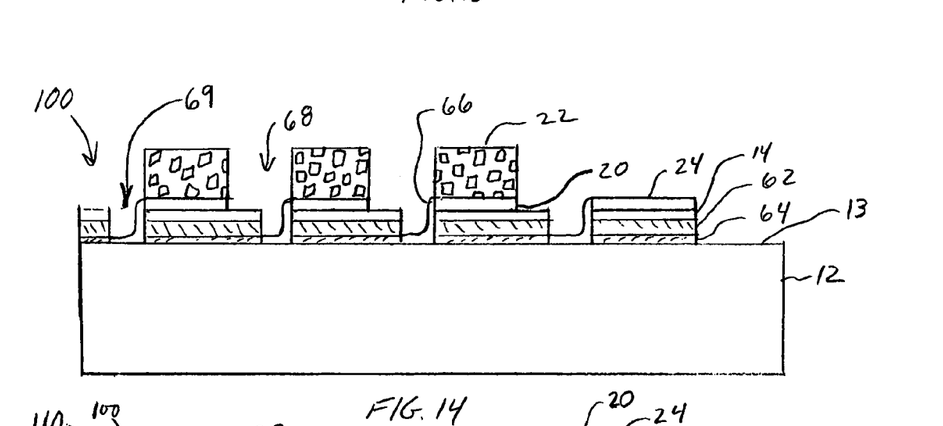

The layer of piezoelectric material 18, bottom electrode layer 16, first dielectric film 14, silicon layer 62, and buried silicon oxide layer 64 are subsequently etched to provide separate piezoelectric elements 22 and a ground pad 24, and to expose the front side 13 of the substrate 12. The piezoelectric 18 and bottom electrode 16 layers are etched to form the pMUT element shape 32 separated by openings 68. The first dielectric 14, thin silicon 62, and buried oxide 64 layers are further etched to form spaced-apart vias 69 exposing the substrate 12. A conductive film 66 is deposited in the spaced-apart vias 69, as illustrated in FIG. 14, to provide electrical connection between the bottom electrode 20 and the through-wafer interconnects to be subsequently formed. Patterning of the pMUT device structure 100 can be done using conventional photolithographic and etching techniques, as previously described. In certain embodiments of the present invention, the conductive film 66 can be any of the metals described above with respect to the bottom electrode 20, top electrode 32, and conformal conductive layer 42.

Figure 15:
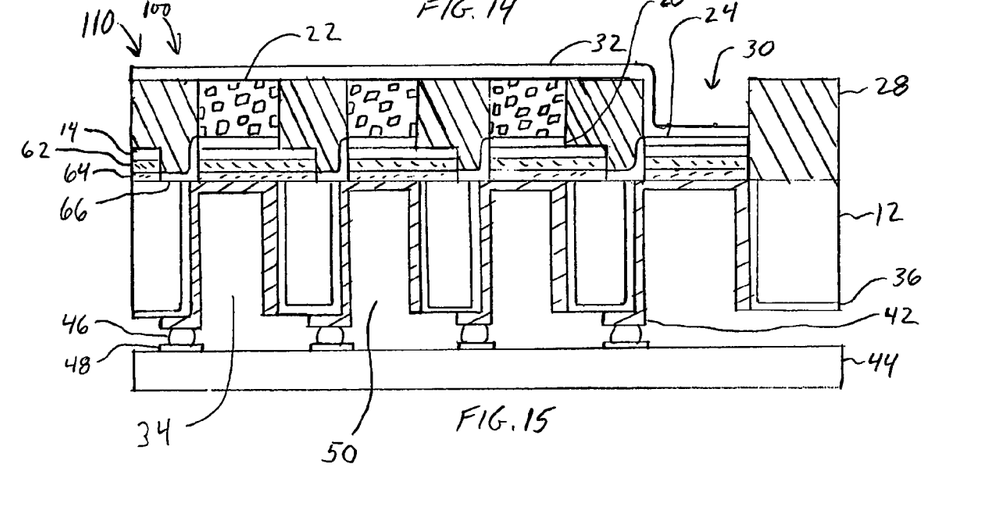

The SOI pMUT device structure 100 is further processed, as previously explained with respect to the other embodiments of pMUT devices, to form the second dielectric film 28, top electrode 32, through-wafer vias 34, conformal insulating layer 36, and conformal conductive film 42, as illustrated in FIG. 15. Electrical contact between the conductive film 66 and the conformal conductive film 42 provide a through-wafer interconnect. The SOI pMUT device structure 100 is connected to a semiconductor device 44, such as through solder bumps 46, as shown in FIG. 15, to form a vertically integrated pMUT device 110. In other embodiments, the semiconductor device 44 can be electrically connected to the conformal conductive film 42 through metal contacts formed in an epoxy layer deposited on the surface of the semiconductor device which attaches the pMUT device to the semiconductor device, as previously described.

Uses for pMUTs formed according to the present invention include real time, three-dimensional intracardiac or intravascular imaging, imaging for minimally invasive or robotic surgeries, catheter-based imaging, portable ultrasound probes, and miniature hydrophones. In certain embodiments of the present invention, the pMUTs are optimized for operation in the frequency range of about 1-20 MHz.

The embodiments illustrated in the instant disclosure are for illustrative purposes. They should not be construed to limit the scope of the claims. As is clear to one of ordinary skill in this art, the instant disclosure encompasses a wide variety of embodiments not specifically illustrated herein.

What is claimed is:

1. A piezoelectric micromachined ultrasonic transducer comprising:
    a substrate having a first surface and second surface opposing the first surface;
    an opening formed through said substrate to form a via in the substrate extending from the first surface of the substrate to the second surface of the substrate;
    a bottom electrode formed on the first surface of said substrate and spanning across said opening at a base of the via on the first surface;
    a piezoelectric element formed disposed above the via and on said bottom electrode; and
    a conformal conductive film formed in contact with the bottom electrode and on a sidewall of the via,
    wherein an open cavity is maintained in the via from the first surface to the second surface.

2. The piezoelectric micromachined ultrasonic transducer according to claim 1, further comprising a conformal insulating film formed on the sidewall of the opening underlying said conformal conductive film.

3. The piezoelectric micromachined ultrasonic transducer according to claim 1, further comprising a first dielectric film formed on said substrate underlying said bottom electrode.

4. The piezoelectric micromachined ultrasonic transducer according to claim 3, further comprising a second dielectric film surrounding said piezoelectric element, wherein top edges of said piezoelectric element are covered with said second dielectric film.

5. The piezoelectric micromachined ultrasonic transducer according to claim 1, further comprising a top electrode in contact with said piezoelectric element.

6. The piezoelectric micromachined ultrasonic transducer according to claim 1, wherein the piezoelectric element is circular in shape.

7. The piezoelectric micromachined ultrasonic transducer according to claim 1, wherein the piezoelectric element is square, rectangular or other polygonal shape.

8. The piezoelectric micromachined ultrasonic transducer according to claim 1, wherein the piezoelectric element has a thickness between 0.5 μm to 100 μm.

9. The piezoelectric micromachined ultrasonic transducer according to claim 1, wherein the piezoelectric element has a lateral dimension between 10 μm to 500 μm.

10. The piezoelectric micromachined ultrasonic transducer according to claim 1, wherein the piezoelectric element is configured to operate at frequencies between 1 and 20 MHz.

11. The piezoelectric micromachined ultrasonic transducer according to claim 1, wherein the piezoelectric element is configured to operate at frequencies greater than 20 MHz.

12. A piezoelectric micromachined ultrasonic transducer comprising:
    a substrate having a first surface and second surface opposing the first surface;
    a first dielectric film formed on the first surface of said substrate;
    an opening extending from the first surface of the substrate to the second surface of the substrate to form a via in the substrate having a sidewall formed through said substrate and first dielectric film;
    a bottom electrode formed on said first dielectric film spanning across said opening at a base of the via on the first surface, with said opening being maintained from the first surface to the second surface;
    a piezoelectric element formed on said bottom electrode and disposed above the via;
    a second dielectric film surrounding said piezoelectric element, wherein top edges of said piezoelectric element are covered with said second dielectric film;
    a conformal insulating film formed on the sidewall of the opening;
    a conformal conductive film formed in contact with the bottom electrode and on the sidewall of the via, wherein an open cavity is maintained in the via; and
    a top electrode formed in contact with said piezoelectric element.

13. A piezoelectric micromachined ultrasonic transducer comprising:
    a substrate having a first surface and second surface opposing the first surface;
    a plurality of openings extending from the first surface of the substrate to the second surface of the substrate to form vias in the substrate having respective sidewalls formed through said substrate;
    spaced-apart bottom electrodes formed on the first surface of said substrate, wherein each spaced-apart bottom electrode spans across one of said plurality of openings at a base of one of the vias on the first surface;
    spaced-apart piezoelectric elements formed on each of said bottom electrodes, and disposed respectively above the vias; and
    a conformal conductive film formed on each of said sidewalls of the plurality of vias,
    wherein each conformal conductive film is in contact with one or more of said bottom electrodes and open cavities are maintained in each of the vias from the first surface to the second surface.

14. The piezoelectric micromachined ultrasonic transducer according to claim 13, further comprising a conformal insulating film formed on each of said sidewalls of the plurality of openings underlying said conformal conductive film.

15. The piezoelectric micromachined ultrasonic transducer according to claim 13, further comprising a first dielectric film formed on said substrate underlying said bottom electrodes.

16. The piezoelectric micromachined ultrasonic transducer according to claim 13, wherein the piezoelectric elements are circular in shape.

17. The piezoelectric micromachined ultrasonic transducer according to claim 13, wherein the piezoelectric elements are square, rectangular or other polygonal shape.

18. The piezoelectric micromachined ultrasonic transducer according to claim 13, wherein the piezoelectric elements form a one-dimensional or two-dimensional array.

19. The piezoelectric micromachined ultrasonic transducer according to claim 15, further comprising a second dielectric film formed between said piezoelectric elements.

20. The piezoelectric micromachined ultrasonic transducer according to claim 19, wherein said second dielectric film is disposed on top edges of said piezoelectric elements.

21. The piezoelectric micromachined ultrasonic transducer according to claim 19, further comprising a ground pad formed on said substrate.

22. The piezoelectric micromachined ultrasonic transducer according to claim 21, further comprising a top electrode in contact with said piezoelectric elements and said ground pad.

23. The piezoelectric micromachined ultrasonic transducer according to claim 22, wherein said top electrode and said conformal conductive film comprise a metal film.

24. The piezoelectric micromachined ultrasonic transducer according to claim 13, wherein the substrate comprises a silicon wafer.

25. The piezoelectric micromachined ultrasonic transducer according to claim 24, wherein said silicon wafer is a silicon-on-insulator wafer including a bulk silicon layer, an insulator, and a Si overlayer, and the opening extends through the bulk silicon layer.

26. A vertically integrated piezoelectric micromachined ultrasonic transducer device comprising a semiconductor device attached to the ultrasonic transducer of claim 13 wherein said conformal conductive film is electrically connected to said semiconductor device.

27. The vertically integrated piezoelectric micromachined ultrasonic transducer device according to claim 26, further comprising a polymer film formed on a surface of the semiconductor device facing the open cavities.

28. The vertically integrated piezoelectric micromachined ultrasonic transducer device according to claim 26, wherein said semiconductor device is a complementary metal oxide semiconductor chip.

29. The vertically integrated piezoelectric micromachined ultrasonic transducer device according to claim 26, further comprising an adhesive layer between said ultrasonic transducer and said semiconductor device.

30. The vertically integrated piezoelectric micromachined ultrasonic transducer device according to claim 29, further comprising metal contacts formed in said adhesive layer electrically connecting said ultrasonic transducer to said semiconductor device.

31. The vertically integrated piezoelectric micromachined ultrasonic transducer device according to claim 26, further comprising solder bumps between said ultrasonic transducer and said semiconductor device.

32. A method of forming a piezoelectric ultrasonic transducer comprising:
    providing a substrate having a first surface and second surface opposing the first surface;
    forming a bottom electrode layer on the substrate;
    forming a layer of piezoelectric material on the bottom electrode layer;
    patterning said bottom electrode layer and layer of piezoelectric material to form a plurality of spaced-apart bottom electrodes and spaced-apart piezoelectric elements on the substrate;

forming an opening extending from the first surface of the substrate to the second surface of the substrate to form vias in the substrate having respective sidewalls through the substrate under each of the plurality of bottom electrodes exposing the bottom electrodes, said spaced-apart piezoelectric elements disposed respectively above the vias; and forming a conformal conductive film on said sidewalls and in contact with said bottom electrodes, with said opening being maintained from the first surface to the second surface.

33. The method according to claim 32, further comprising forming a conformal insulating film on the sidewalls before forming the conformal conductive film.

34. The method according to claim 32, further comprising forming a first dielectric film on the substrate before forming the plurality of spaced-apart bottom electrodes.

35. The method according to claim 34, further comprising forming a second dielectric film between the piezoelectric elements.

36. The method according to claim 35, further comprising forming a ground pad on said substrate.

37. The method according to claim 36, further comprising forming a top electrode in contact with said piezoelectric elements and said ground pad.

38. The method according to claim 37, wherein said top electrode and said conformal conductive film comprise metal films.

39. The method according to claim 32, wherein the substrate comprises a silicon wafer.

40. The method according to claim 39, wherein said silicon wafer is a silicon-on-insulator wafer including a bulk silicon layer, an insulator, and a Si overlayer, and the opening extends through the bulk silicon layer.

41. The method according to claim 32, further comprising attaching a semiconductor device to said ultrasonic transducer wherein said conformal conductive film is in electrical contact with the semiconductor device.

42. The method according to claim 41, further comprising forming a polymer film on a surface of the semiconductor device facing the openings having sidewalls.

43. The method according to claim 42, wherein the polymer film forms an adhesive layer between said ultrasonic transducer and said semiconductor device.

44. The method according to claim 42, further comprising forming metal contacts in said polymer film.

45. The method according to claim 41, further comprising forming solder bumps between said ultrasonic transducer and said semiconductor device.

46. The method according to claim 32, wherein at least one of the forming a bottom electrode layer, the forming a layer of piezoelectric material, the patterning the bottom electrode layer and the layer of piezoelectric material, the forming an opening through the substrate, and the forming a conformal conductive film is a lithographic process.

47. The method according to claim 32, wherein the forming a bottom electrode layer, the forming a layer of piezoelectric material, the patterning the bottom electrode layer and the layer of piezoelectric material, the forming an opening through the substrate, and the forming a conformal conductive film are lithographic processes.

48. A vertically integrated piezoelectric micromachined ultrasonic transducer device comprising:
a substrate having a first surface and second surface opposing the first surface;
a plurality of openings extending from the first surface of the substrate to the second surface of the substrate to form vias in the substrate having respective sidewalls formed through said substrate;
a first dielectric film formed on said substrate;
spaced-apart bottom electrodes formed on said first dielectric film; each spaced-apart bottom electrode spanning across one of said plurality of openings at a base of one of the vias on the first surface, with said opening being maintained from the first surface to the second surface;
spaced-apart piezoelectric elements formed on each of said bottom electrodes, and disposed respectively above the vias;
a conformal insulating film formed on each of said sidewalls of the plurality of openings;
a conformal conductive film formed on each of said conformal insulating films,
wherein each conformal conductive film is in contact with one or more of said bottom electrodes, and an open cavity is maintained in each of the vias;
a ground pad formed on said substrate; a second dielectric film formed between said piezoelectric elements;
a top electrode in contact with said piezoelectric elements and said ground pad; and
a semiconductor device attached to said ultrasonic transducer, wherein said conformal conductive film is electrically connected to said semiconductor device.

49. The vertically integrated piezoelectric micromachined ultrasonic transducer device according to claim 48 further comprising spaced-apart vias formed through said first dielectric film and through a portion of said substrate.

50. The vertically integrated piezoelectric micromachined ultrasonic transducer device according to claim 49, further comprising metallization in said spaced-apart vias providing electrical contact between said bottom electrode and said conformal conductive film.

51. The vertically integrated piezoelectric micromachined ultrasonic transducer device according to claim 48, further comprising a polymer film formed on a surface of the semiconductor device facing the open cavities.

52. The vertically integrated piezoelectric micromachined ultrasonic transducer device according to claim 51, wherein said semiconductor device is a complementary metal oxide semiconductor chip.

53. The piezoelectric micromachined ultrasonic transducer according to claim 48, wherein the substrate comprises a silicon wafer.

54. The piezoelectric micromachined ultrasonic transducer according to claim 53, wherein said silicon wafer is a silicon-on-insulator wafer including a bulk silicon layer, an insulator, and a Si overlayer, and the opening extends through the bulk silicon layer.

55. The piezoelectric micromachined ultrasonic transducer device according to claim 48, further comprising an adhesive layer between said ultrasonic transducer and said semiconductor device.

56. The-piezoelectric micromachined ultrasonic transducer device according to claim 55, further comprising metal contacts formed in said adhesive layer electrically connecting said ultrasonic transducer to said semiconductor device.

57. The piezoelectric micromachined ultrasonic transducer device according to claim 48, further comprising solder bumps between said ultrasonic transducer and said semiconductor device.

58. The piezoelectric micromachined ultrasonic transducer device according to claim 48, wherein each of the plurality of piezoelectric elements can be operated independently, all elements can be operated simultaneously, or subsets of elements can be electrically connected to form larger independently operated subsets of elements in an array.

59. A method of forming a vertically integrated piezoelectric micromachined ultrasonic transducer device comprising:
providing a substrate having a first surface and second surface opposing the first surface;
forming a first dielectric layer on the substrate;
forming a bottom electrode layer on the first dielectric layer;
forming a layer of piezoelectric material on the bottom electrode layer;
patterning said bottom electrode layer and said layer of piezoelectric material to form a plurality of spaced-apart bottom electrodes and spaced-apart piezoelectric elements on the substrate;
forming a ground pad on said substrate; forming a second dielectric layer between the piezoelectric elements;
forming a top electrode in contact with said piezoelectric elements and said ground pad;
forming openings extending from the first surface of the substrate to the second surface of the substrate to form vias having respective sidewalls through the substrate under each of said spaced-apart bottom electrodes and piezoelectric elements, said spaced-apart piezoelectric elements disposed respectively above the vias;
forming a conformal insulating layer on the sidewalls of said openings;
forming a conformal conductive layer on said conformal insulating layer and in contact with each of said bottom electrodes, with the openings being maintained from the first surface to the second surface; and
attaching a semiconductor device to said ultrasonic transducer through said conformal conductive layer.

60. The method according to claim 59, wherein the substrate comprises a silicon wafer.

61. The method according to claim 60, wherein said openings are also formed through said first dielectric layer exposing said bottom electrodes.

62. The method according to claim 60, wherein said silicon wafer is a silicon-on-insulator wafer including a bulk silicon layer, an insulator, and a Si overlayer, and the opening extends through the bulk silicon layer.

63. The method according to claim 62, further comprising forming spaced-apart vias through said first dielectric layer and through a portion of said silicon-on-insulator wafer.

64. The method according to claim 63, further comprising forming a metal layer in each of said spaced-apart vias providing electrical contact with the bottom electrode.

65. The method according to claim 64, wherein said openings expose the metal layer in said spaced-apart vias, and the conformal conductive layer is deposited such that it is in electrical contact with the metal layer in the spaced-apart vias.

66. The method according to claim 59, further comprising forming a polymer film on a surface of the semiconductor device facing the openings having sidewalls.

67. The method according to claim 66, wherein the polymer film forms an adhesive layer between said ultrasonic transducer and said semiconductor device.

68. The method according to claim 66, further comprising forming metal contacts in said polymer film.

69. The method according to claim 59, further comprising forming solder bumps between said ultrasonic transducer and said semiconductor device.

70. The piezoelectric micromachined ultrasonic transducer according to claim 9, wherein a first piezoelectric element is spaced apart from a second piezoelectric element by a center-to-center spacing between 15 μm to 1000 μm.

71. A piezoelectric micromachined ultrasonic transducer comprising:
a substrate;
an opening formed in the substrate to form a via in the substrate;
a bottom electrode formed on said substrate and spanning said opening at a base of the via;
a piezoelectric element formed on the bottom electrode to be disposed above the via;
a conformal conductive film formed in contact with the bottom electrode and on a sidewall of the via, and
an open cavity maintained in the via adjacent the conformal conductive film on the sidewall.

* * * * *

UNITED STATES PATENT AND TRADEMARK OFFICE
CERTIFICATE OF CORRECTION

| | |
|---|---|
| PATENT NO. | : 7,449,821 B2 |
| APPLICATION NO. | : 11/068776 |
| DATED | : November 11, 2008 |
| INVENTOR(S) | : David Edward Dausch |

It is certified that error appears in the above-identified patent and that said Letters Patent is hereby corrected as shown below:

In the Specification

In Column 1, before the heading "TECHNICAL FIELD OF THE INVENTION" please add the following heading and paragraph:
FEDERALLY SPONSORED RESEARCH OR DEVELOPMENT
This invention was made with government support under R33 EB000566, and R21 EB000566 awarded by the National Institutes of Health. The government has certain rights in the invention.

Signed and Sealed this
Eighth Day of August, 2023

Katherine Kelly Vidal
*Director of the United States Patent and Trademark Office*